US010420345B2

(12) United States Patent
Clapsaddle et al.

(10) Patent No.: US 10,420,345 B2
(45) Date of Patent: Sep. 24, 2019

(54) HUMIDITY TOLERANT CARBON DIOXIDE GENERATOR FOR ARTHROPOD TRAP AND METHOD OF USING SAME

(71) Applicant: TDA Research, Inc, Wheat Ridge, CO (US)

(72) Inventors: Brady Clapsaddle, Littleton, CO (US); Joe Fredrickson, Denver, CO (US); William Bell, Boulder, CO (US); Trevor Haanstad, Denver, CO (US); Jeff Martin, Arvada, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 0 days.

(21) Appl. No.: 15/805,850

(22) Filed: Nov. 7, 2017

(65) Prior Publication Data

US 2019/0133134 A1    May 9, 2019

(51) Int. Cl.
*A01N 59/04* (2006.01)
*B65D 83/04* (2006.01)
*A01M 1/02* (2006.01)
*A01M 1/10* (2006.01)

(52) U.S. Cl.
CPC ............. *A01N 59/04* (2013.01); *A01M 1/023* (2013.01); *A01M 1/10* (2013.01); *B65D 83/04* (2013.01)

(58) Field of Classification Search
CPC ......... A01N 59/04; A01N 59/00; A01M 1/23; A01M 1/00
See application file for complete search history.

(56) References Cited

U.S. PATENT DOCUMENTS

| 6,209,256 | B1 * | 4/2001 | Brittin | A01M 1/023 43/107 |
| 8,475,783 | B2 * | 7/2013 | Prohaska | A01N 59/04 424/84 |
| 2010/0287816 | A1 * | 11/2010 | Abelbeck | A01M 1/023 43/113 |
| 2011/0049198 | A1 * | 3/2011 | Muth | G01F 11/24 222/636 |
| 2013/0142753 | A1 * | 6/2013 | Prohaska | A01N 59/04 424/84 |

OTHER PUBLICATIONS

Malveau, Biomacromolecules, 3, 2002 (Year: 2002).*

* cited by examiner

*Primary Examiner* — Susan T Tran
*Assistant Examiner* — William Craigo
(74) *Attorney, Agent, or Firm* — Brian J. Elliott

(57) ABSTRACT

The present invention provides a humidity tolerant $CO_2$ generator that operates in combination with an arthropod trap. The $CO_2$ generator comprises a means for controllably adding solid pellets to an aqueous acid solution, and optionally includes a sound-based counting system for counting the number of pellets dispensed from a feeder reservoir and into a reaction chamber. The invention also provides a method of using the same.

2 Claims, 13 Drawing Sheets

HUMIDITY TOLERANT CARBON DIOXIDE GENERATOR FOR ARTHROPOD TRAP AND METHOD OF USING SAME

STATEMENT REGARDING FEDERALLY SPONSORED RESEARCH OR DEVELOPMENT

This invention was made using U.S. government funding through the U.S. Defense Health Program (DHP) SBIR Phase II contract #FA8650-15-C-6617. The government has certain rights in this invention.

FIELD OF THE INVENTION

The field of the invention relates to a carbon dioxide generator attached to an insect trap.

BACKGROUND

It is desirable to be able to reproducibly sample populations of arthropod disease vectors (e.g., mosquitoes, sandflies, ticks and fleas), both to monitor their size and to allow analysis of the trapped arthropods to determine the presence of human diseases (e.g., malaria, dengue, Zika, West Nile Virus, Lyme disease) in the population. Many arthropod disease vectors are attracted to carbon dioxide ($CO_2$). It is common to trap arthropods for a period of about 12 hours, for example from around sunset to around sunrise, because sunset and sunrise are times are when many disease vectors are active. The vector trap and the accompanying $CO_2$ source must operate unattended, and the source must produce the target flow rate of $CO_2$ over that time period. Known $CO_2$ sources include pressure cylinders of $CO_2$ and dry ice. However, these $CO_2$ sources may not be available in all locations. As an alternative, $CO_2$ can be produced at the site of the trap by mixing a carbonate or bicarbonate salt (for example, sodium bicarbonate) and an acid (for example, citric acid). Systems that operate on this principle include that described by Prohaska (U.S. Pat. No. 8,475,783 B2, Jul. 2, 2013).

Reliable operation of $CO_2$ generators using this approach depends on combining the two reactants at a rate that will consistently produce the target amount of $CO_2$. It is desirable that the components react to produce the $CO_2$ rapidly, because any delay in the production of $CO_2$ after combining the reactants may interfere with the desired steady production of $CO_2$, and will complicate the timing of the addition of components. Consistent with this objective, portable $CO_2$ generators that use one component in a solid form (not a liquid or a liquid solution) have used the material as a powder solid. The small particle size of a powder allows the material to dissolve rapidly in the water solution containing the other component or components. Bicarbonate or carbonate salts are commercially available as powder solids so that no additional processing is required. Additional processing is undesirable because it adds to the cost of the consumable material, and requires the manufacturer of the consumable supplies to carry an inventory of a processed material. Consistent with these considerations, systems using on-site generation of $CO_2$ for vector trapping use mixing of a powder solid with a water solution. For example, see Prohaska (2013).

The prior art teaches that it is important to use powdered salts so that an even and measured $CO_2$ generation rate can be achieved, while at the same time identifying problems associated with the actual use of powders in unattended systems. For example, in U.S. Pat. No. 6,920,716, Kollars et al. disclose a non-electrical carbon dioxide generating arthropod trap. In this disclosure the combination of baking soda and vinegar is used to generate carbon dioxide gas with the optional addition of urea, lactic acid, and ammonia as further attractants. In this device the dry sodium bicarbonate powder (baking soda) is placed in a separate reactor container and aqueous solution of acetic acid (vinegar) is dripped into the reactor container to produce carbon dioxide. However, this method of mixing the reactants leads to powder caking and inconsistent gas flow rates.

Prohaska et al. teaches a potential solution to the problem of using powdered salts. U.S. Pat. No. 8,475,783 B2 teaches a device for generating carbon dioxide as an attractant for biting arthropods in combination with a trap, comprising: a reaction chamber charged with an aqueous acid solution when in use; a gas outlet from the reaction chamber connecting between the reaction chamber and the trap; a feeder reservoir containing a powder when in use, said powder comprising a bicarbonate salt; and means for controllably adding the powder from the feeder reservoir to the reaction chamber; whereby carbon dioxide is generated in the reaction chamber, passed through the outlet and into the trap. Further disclosed is an improved arthropod trap for catching biting arthropods assisted by the evolution of carbon dioxide, the improvement comprising: a reaction chamber charged with an aqueous acid solution when in use; a gas outlet from the reaction chamber connecting between the reaction chamber and the trap; a feeder reservoir containing a powder when in use, said powder comprising a bicarbonate salt; and means for controllably adding the powder from the feeder reservoir to the reaction chamber; whereby carbon dioxide is generated in the reaction chamber, passed through the outlet and through or into the trap.

Prohaska further admits potential problems when operating solid powder fed traps in humid conditions. He teaches that the powder comprising a bicarbonate salt may further comprise additives that permit flow of the powder in humid conditions. These include anti caking agents such as silicon dioxide, aluminum oxide, boron nitride, calcium chloride, magnesium sulfate, calcium bentonite, sodium bentonite, sodium alumino-silicate, magnesium carbonate, calcium silicate, tricalcium phosphate, talc, kaolin, starch, cellulose or combinations thereof. In addition to adding anti-caking agents to the powder comprising a bicarbonate salt, Prohaska states that it may be necessary to heat the powder before it is released into the reaction vessel to a temperature of 35° C. immediately prior to use to prevent caking in humid conditions.

The arthropod traps of the prior art suffer from at least one of the following limitations: powdered reagents are required to adequately meter the solid into the water solution and to result in controllable $CO_2$ generation rates, they suffer from poor performance in humid conditions due to caking of powders and poor solid metering control.

BRIEF SUMMARY OF THE INVENTION

The present invention solves the limitations of the prior art and provides an arthropod trap using controlled pellet metering for accurate $CO_2$ generation in humid environments. The present invention teaches an apparatus to produce a steady stream of gas over an extended period (for example, up to 12 hours) in a portable apparatus. The gas is produced by adding a solid in pellet form to a liquid, and comprises a system to control the addition rate of the pellets to produce the desired flow rate of gas. In one embodiment, the addition rate of the pellets is controlled by counting each pellet by the sound produced as it is added to the liquid, and using an algorithm to determine the optimum rate of addition to produce the desired flow rate of gas.

The present invention provides a device for generating carbon dioxide as an attractant for biting arthropods in combination with a trap, comprising: a reaction chamber charged with an aqueous acid solution when the $CO_2$ generator is in use; a trap for biting arthropods; a gas outlet from the reaction chamber connecting between the reaction chamber and the trap for biting arthropods; a feeder reservoir containing a plurality of pellets when in use, said pellets comprising a bicarbonate salt; and a means for controllably adding the pellets from the feeder reservoir to the reaction chamber; whereby carbon dioxide is generated in the reaction chamber, passed through the outlet and into the trap for biting arthropods. In optional embodiments the device further comprises: a sound bar; a microphone sensor; and a means for counting the pellets added to the reaction chamber when in use. In further optional embodiments, the device also comprises a resonant sound board connected to the sound bar; and a sound absorbing material surrounding the microphone sensor and the resonant sound board; wherein, the resonant sound board is physically attached to the sound bar and transfers sound from the sound bar to the microphone sensor; and, wherein the sound absorbing material reduces external noise reaching the microphone sensor.

In a preferred embodiment the feeder reservoir is a rotating vessel comprising a hole for pellet dispensing, wherein the hole is self-unclogging by the action of gravity on the pellets during rotation of the feeder reservoir while in use. Preferably, the feeder reservoir is a hemispherical rotating feeder with at least one dispensing hole, wherein the diameter of the at least one dispensing hole is from 1.75 to 1.95 times the average diameter of the plurality of pellets.

In an embodiment the aqueous solution comprises one or more acids, wherein at least one of the one or more acids is chosen from acetic acid, ascorbic acid, butanoic acid, citric acid, formic acid, heptanoic acid, hexanoic acid, 1-octanoic acid, lactic acid, octanoic acid, oxalic acid, pentanoic acid, propanoic acid, uric acid, succinic acid, malonic acid, maleic acid, citriconic acid, norbornene dicarboxylic acid, gamma-hydroxy butanoic acid, benzoic acid, boric acid sulfuric acid, hydrochloric acid, nitric acid, phosphoric acid, linear or branched $C_1$-$C_{20}$ alkane sulfonic acids, linear or branched $C_2$-$C_{20}$ alkene sulfonic acids, $C_6$-$C_{20}$ substituted or unsubstituted aryl sulfonic acids or combinations thereof. Optionally, the acid may comprise ammonium bisulfate other bisulfate salts (sodium, lithium, potassium), or mixtures thereof.

In another embodiment the pellets comprise a bicarbonate salt, chosen from sodium bicarbonate, lithium bicarbonate, potassium bicarbonate, ammonium bicarbonate, magnesium bicarbonate, calcium bicarbonate strontium bicarbonate or combinations thereof. Preferably, the pellets further comprise a binder and the binder is either a wax, a magnesium stearate, a starch, a lignin, a cellulosic binder, a clay or a polymeric binder. In other embodiments, the pellets comprise a pelletizing lubricant, for example talc, magnesium stearates, hexagonal boron nitride, amide wax, polytetrafluoroethylene or tungsten disulfide.

In preferred embodiments, the pellets used in the present invention each have a mass within 10 weight percent of the arithmetic mean pellet mass.

The present invention also provides a method of generating carbon dioxide as an attractant for biting arthropods connected to an insect trap, comprising the steps of: providing a reaction chamber charged with an aqueous acid solution; providing a trap for biting arthropods; providing a gas outlet from the reaction chamber for connecting between the reaction chamber and the trap for biting arthropods; providing a feeder reservoir containing a plurality of pellets, said pellets comprising a bicarbonate salt; and providing means for controllably adding the pellets from the feeder reservoir to the reaction chamber; wherein carbon dioxide is generated in the reaction chamber, passed through the outlet and into the trap for biting arthropods. Optionally the method also comprises the steps of: providing a sound bar; providing a microphone sensor; and providing a means for counting the pellets added to the reaction chamber when in use.

In optional embodiments, the method uses an aqueous acid solution, comprising one or more acids chosen from acetic acid, ascorbic acid, butanoic acid, citric acid, formic acid, heptanoic acid, hexanoic acid, lactic acid, octanoic acid, oxalic acid, pentanoic acid, propanoic acid, uric acid, succinic acid, malonic acid, maleic acid, citriconic acid, norbornene dicarboxylic acid, gamma-hydroxy butanoic acid, benzoic acid, boric acid sulfuric acid, hydrochloric acid, nitric acid, phosphoric acid, linear or branched $C_1$-$C_{20}$ alkane sulfonic acids, linear or branched $C_2$-$C_{20}$ alkene sulfonic acids, $C_6$-$C_{20}$ substituted or unsubstituted aryl sulfonic acids or combinations thereof. Optionally, the acid may comprise ammonium bisulfate other bisulfate salts (sodium, lithium, potassium), or mixtures thereof.

In optional embodiments, the method uses a bicarbonate salt chosen from sodium bicarbonate, lithium bicarbonate, potassium bicarbonate, ammonium bicarbonate, magnesium bicarbonate, calcium bicarbonate strontium bicarbonate or combinations thereof. Optionally the pellets further comprise a carbonate salt chosen from sodium carbonate, lithium carbonate, potassium carbonate, ammonium carbonate, magnesium carbonate, calcium carbonate strontium carbonate or combinations thereof. The method may use pellets further comprises a binder and a pelletizing lubricant or where the pellets each have a mass within 10 weight percent of the arithmetic mean pellet mass. The method may further comprise the step of adding an anhydrous salt or a partially hydrated salt to the aqueous acid solution to adjust the temperature of the solution prior to adding the pellets.

DETAILED DESCRIPTION OF THE INVENTION

Figure 1:
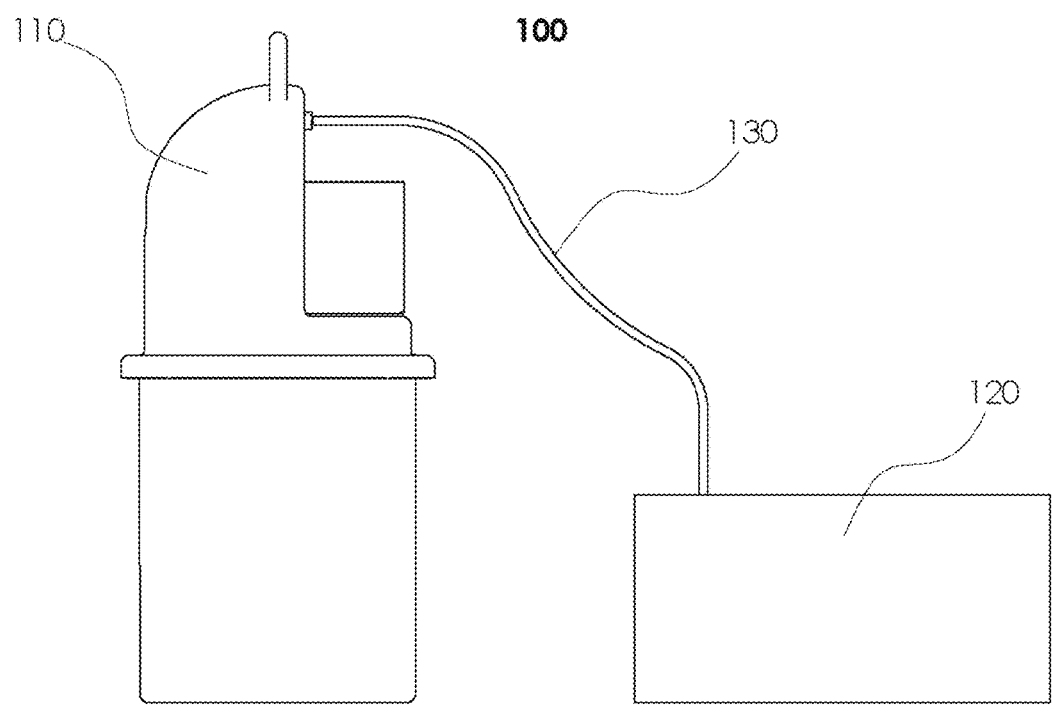
FIG. 1. Humidity tolerant $CO_2$ generator connected to an arthropod trap.

In our efforts to develop a portable $CO_2$ generator, we discovered that devices using a powder feeding approach sometimes fail to feed the powder consistently. Surprisingly, we found that converting a sodium bicarbonate powder to solid pellets gave more reliable feeding. The pellets that worked well included ¼ inch diameter cylinders having a length of 6 mm, or alternatively a length of ¼ inch. This agglomeration step required use of equipment and additives as described in a later section.

Having produced pellets of one of the components (for example, sodium bicarbonate), we discovered an additional advantage of feeding pellets rather than powders. Our invention places a plate of metal or other suitable material in the path that the pellets follow from the feed hopper to the reactor. When the pellets impact on the plate, each pellet makes a noise, which can be recorded by a microphone. Using signal processing hardware on an electronic circuit (further defined below) and suitable software, the number of pellets can be counted. In this way, our process determines how many pellets of material (all of which are approximately the same size) are being added to the solution over a given time period. In contrast, $CO_2$ generators of the previous art simply operate the mechanical components of the feed system at a controlled rate, with the assumption that the powder will be fed consistently at a rate determined by the operation of the mechanical components. Because that consistent feeding is not always the case, it is desirable to have information on the amount of the material that is actually added to the reaction vessel. Monitoring the sound of the pellets as they strike a sound-generating plate provides immediate and usable information on the amount of the material that is actually added to the reaction vessel.

Use of pellets or other agglomerates thus provides two advantages: improved reliability of feeding, and a convenient and inexpensive means to follow the actual rate of addition of material.

Further, the composition of the liquid may change over the course of the generation process. For example, the pH of the solution may change, which in turn affects both the rate of dissolution of added solid and the rate and extent of reaction. Therefore, the rate of addition at any point during the 12-hour production of $CO_2$ may need to be adjusted in response to the amount of the components that have actually been mixed at that time. Monitoring the rate of addition by monitoring the sound produced as the pellets are added allows for accurate adjustments to the rate of pellet addition.

In the claims the term "trap for biting arthropods" means any arthropod trapping configuration or device that can utilize $CO_2$ attractant to bring the arthropod to the capturing mechanism of the trap. Such traps can be user fabricated, or include commercial traps available for sale. Examples of traps include, but are not limited to, CDC light traps (in various configurations with various light sources or with no light source), Fay-Prince Traps, CDC Gravid Traps, New Jersey light traps, sticky traps and fly papers, Ifakara and other tent traps, BG Sentinel™ traps, myFleaTrap™, and tick traps including pitfall and sticky traps.

In the claims, "pellets" are a compressed mass of a substance or compressed mass of a mixture of substances. Pellets may be defined as any reproducibly agglomerated or compacted solid. The pellets of the present invention may have shapes including cylinders, spheres, cubes, and other known pellet shapes. Pellets are generally small, typically not more than one half inch in size. The singular "pellet" refers to one, whereas a "plurality of pellets" refers to many.

In the claims, the term "microphone sensor" means a device for converting sound waves into an electrical signal that can be transmitted to an electronic circuit, or equivalents thereof.

In the claims, the term "sound bar" means a body that can emit sound waves when a pellet strikes it.

In the claims the term "resonant sound board" means a suitable body that when physically connected by other solid materials to the sound bar can generate sound waves that originated from the sound bar. Specifically, the sound of the pellet striking the sound bar causes sound waves to travel through solid materials to the resonant sound board. The sound waves may travel directly from the resonant sound board to the solid components of a microphone sensor, if the microphone sensor is mounted in direct contact with the resonant sound board.

In the claims the term "a means for" is to be interpreted to include all of the specific examples in the Specification.

In the specification and the claims the term "electronic circuit" means electronic content monitoring chips, solid state devices, programmable devices, a voltage input card and a personal computer, a small electronic device and a portable power source, a programmable chip, an electronic chip, computers, personal computers, electronic monitoring chips, solid state electronics, hard-wired electronics, programmable electronic devices, or equivalents thereof.

An embodiment of the present invention is a device for generating $CO_2$ at programmable flow rates typically, but not limited to, 200 to 400 mL/minute, from the reaction of bicarbonate salt (herein referred to as "bicarbonate") pellets and an aqueous acidic solution. In one example the device may be comprised of a sealed vessel, a bicarbonate pellet dispenser, also called a feeder reservoir herein, with a means for precisely controlling pellet dispensing, and a reaction chamber where acid solution and bicarbonate pellets are mixed to produce carbon dioxide gas. The $CO_2$ gas is produced and released from the generator at a predetermined rate from an outlet of the reactor and can be delivered to an arthropod trap of choice and used as an attractant for luring biting arthropods to the trap.

The $CO_2$ generator of the present invention produces $CO_2$ gas from a chemical reaction between a bicarbonate, for example, sodium bicarbonate ($NaHCO_3$; baking soda), and an aqueous solution of an organic acid (for example, but not limited to, citric acid, lactic acid, malic acid, or equivalents thereof) according to the chemical reaction shown in Scheme 1, where M is a cation of a bicarbonate ($HCO_3^-$) salt. R(COOH) is a water-soluble organic acid, and x represents the number of moles of $CO_2$ gas produced from the reaction $$xMHCO_3(s) + R(COOH)_x(aq) \rightarrow xCO_2(g) + M_x(ROO)_x(aq) + xH_2O \qquad \text{Scheme 1}$$

An illustration of the device that dispenses bicarbonate to the acid solution to produce $CO_2$ gas that is delivered through an outlet to a trap is shown in FIGS. 1-6. The $CO_2$ generator consists of a closed system with a single gas outlet that is directed toward an arthropod trap. Additional configurations with more than one outlet and/or trap are possible. The closed system consists of an air-tight housing, a pellet dispenser and a chemical reactor in which the pellet feeder and reaction chamber are open to each other inside the sealed vessel. The feeder consists of mechanical and electronic control mechanisms, and the bottom consists of a reactor that holds aqueous acid solution and in which the $CO_2$-generating chemical reaction occurs.

The generator operates by dropping pellets of bicarbonate from the pellet dispenser into the organic acid solution in the reactor, or reaction chamber. Once dispensed to the acid solution, the bicarbonate reacts with the acid to form $CO_2$ gas, which then exits through the gas outlet in the top and which can be connected to an external tube that is used to direct the $CO_2$ gas flow to the desired location at an arthropod trap.

The dispensing of bicarbonate pellets to the acid solution is performed precisely through electronic control of the dispensing mechanism. The dispensing mechanism can include, but is not limited to, funneling mechanisms, rotary mechanisms, hopper mechanisms, piston feeder mechanisms, and other pellet feeding mechanisms that are known in the art. Pellets are dispensed to the acid solution in the reactor at a rate that will produce $CO_2$ at a flow rate that is preprogrammed into the electronic dispenser controller. Based on the programmed flow rate, electronic control of pellet dispensing is carried out by a control algorithm that uses variables such as solution pH, amount of bicarbonate dosed, pellet weight, pellet dissolving rate, and the concentration of unreacted acid to determine the number of pellets that need to be dosed to maintain the preprogrammed flow rate of $CO_2$. The key to the operation of the control algorithm is input from the dosing mechanism that provides the number of pellets dosed to the acid solution during $CO_2$ generation. The algorithm takes the input amount of bicarbonate already dosed to the acid solution and then, based on chemical kinetic models and dissolving rates of the bicarbonate pellets, estimates the number of pellets that need to be dosed per unit time to produce the amount of $CO_2$ needed to maintain the pre-programmed flow rate. The rate of pellet dosing is also adjusted over the time of the run based on the increase in pH of the acid solution as the acid becomes spent in the reactor.

Figure 13:
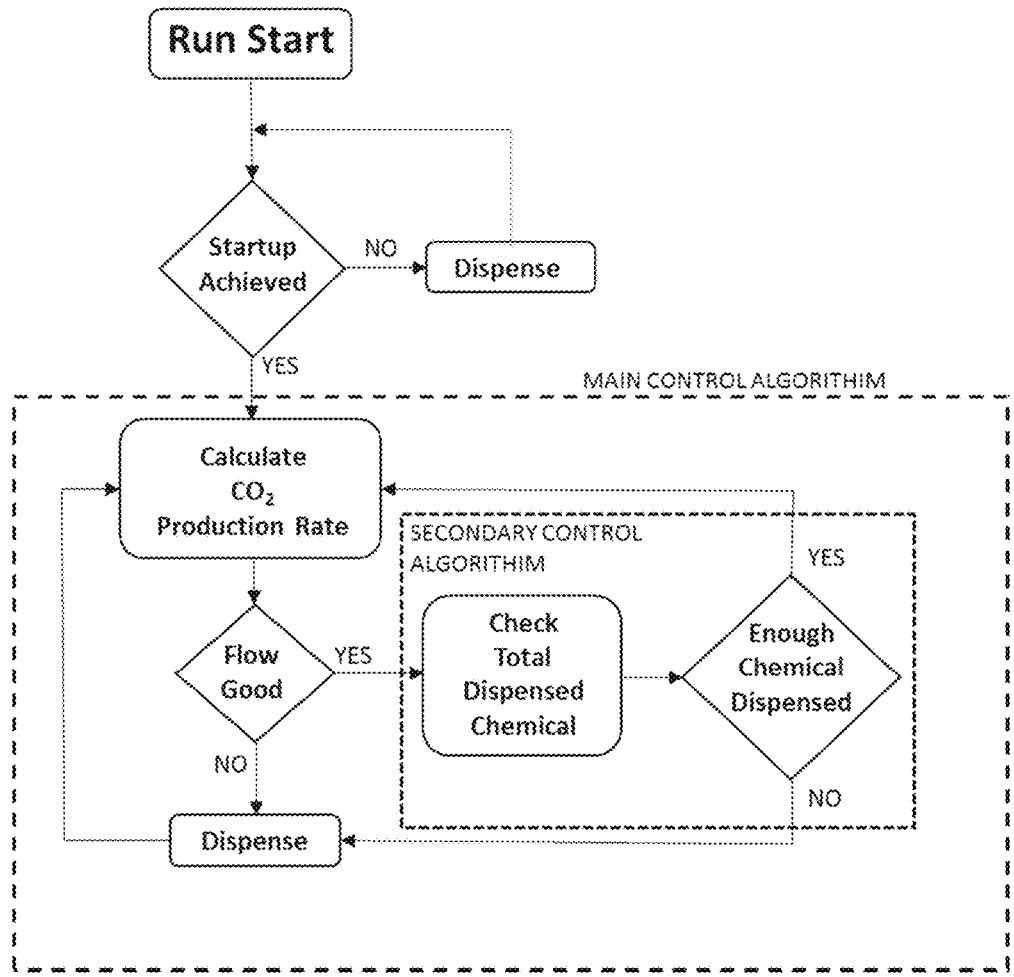
FIG. 13. Control algorithm.

There are two functions that control the $CO_2$ generator: the "main control algorithm" and a "secondary control algorithm" (see FIG. 13). The main algorithm uses a titration calculation that determines the $CO_2$ production based off the reaction chemistry of the two components that are combined in the reactor of the generator. When initiated the microcontroller first runs through a startup routine and dispenses a predetermined amount of chemical to produce a fast start. After the startup routine the microcontroller continually calculates how much chemical needs to be dispensed based off the calculated reaction rate and the required $CO_2$ production rate required. As the generator dispenses one of the reactants into the reactor the microcontroller uses an audio signature to determine how much reactant is dispensed as a feedback mechanism. The unit will continue to dispense the reactant until it reaches an algorithm-calculated $CO_2$ production level above the required rate and drop into a wait cycle as the chemicals react. When the calculated $CO_2$ production rate falls below the required rate the system will start dispensing again until the calculated flow rate is achieved once again. In the flowchart illustrated in FIG. 13, the logic operator "flow good" means the algorithm asks the logic question: is the calculated $CO_2$ flow above the level required for operation of the insect trap at that time? This main control algorithm is followed for the duration of the program run time. The secondary control algorithm works as a "watch dog" to guarantee that all the chemicals are dispensed over the duration of the run. During operation, small time shifts and periods of low flow during dispensing cycles might allow for the feeder reservoir to not fully dispense all the pellets required because the main control algorithm calculates only current production needs. The secondary control algorithm uses a linear function to prevent the generator from under dispensing at any point in the generation cycle and maintains a reproducible generation pattern.

In a preferred embodiment, the device comprises a pellet counter. The input provided to the dosing control algorithm is obtained via a pellet counting mechanism that counts pellets as they are dispensed from the pellet dispenser at the algorithm-determined dose rate. This pellet counter consists of a physical sensor that can then electronically convert a signal produced by dispensing of a single pellet into an electronic signal that can be compiled by the algorithm to keep track of the number of pellets dispensed during a run. The sensor in the pellet counting mechanism can be, but is not limited to, a light sensor, a piezo-electric sensor, a vibration sensor, a sound sensor or microphone, and other equivalents thereof. Using the input from the pellet counter, the electronic control algorithm calculates a pellet dosing rate and the pellets are added at an accurate rate to produce the desired flow rate of $CO_2$. Dispensing of pellets occasionally results in more than one pellet dispensing per mechanical action of the dispenser (for example, per rotation of a hemispherical feeder with a dispensing hole). Zero, one, two, or more pellets may exit the dispenser for a given dispensing attempt. Thus, it is critical to count the pellets that are actually dispensed at each dispensing event or actuation of the dispenser.

In a preferred embodiment, the $CO_2$ generator produces $CO_2$ at a flow rate of 400 mL/minute for twelve hours using 2 kg of starting chemicals (bicarbonate and acid). Flow rates can be adjusted through programming of the algorithm, but run times will vary proportionally with the programmed flow rate, as the amount of chemicals the generator will hold is constant. For example, if the programmed flow rate is increased to 800 mL/minute, the run time will drop from 12 hours to 6 hours. Or, if the flow rate is decreased to 200 ml/minute, the run time will increase to 24 hours. Once loaded with chemicals, the generator is turned on and the $CO_2$ produced is delivered via a tube or equivalent conduit to the insect trap.

Use of pellets in the $CO_2$ generator, especially for humid environments:

The use of pellets in the $CO_2$ generator is necessary for proper operation of the $CO_2$ generator and control of the $CO_2$ flow from the generator, especially in humid environments where the use of powders is problematic as described above. Although not wishing to be bound by theory, in a preferred embodiment the $CO_2$ generator uses pelletized sodium bicarbonate ($NaHCO_3$) that is dispensed into an aqueous acid solution to produce $CO_2$ gas according to Scheme 1. Since the electronic control algorithm needs to know the amount of bicarbonate dosed to calculate the acid solution pH to subsequently calculate a pellet dosing rate at any given time during the run to maintain a pre-programmed flow rate, the use of pellets is preferred as the uniformity (weight, size, density) of a mass-produced pellet is more reproducible than a dispensed powder. Additionally, pellets are necessary in order to physically perturb a pellet counting mechanism that allows the amount of bicarbonate dispensed to be measured and input into the electronic control algorithm (as described above). Powders do not possess the size or mass necessary to trigger a counting device of the type employed in the present device, and powders do not dispense in reproducible amounts during each dosing cycle, especially when exposed to humid environments that cause them to cake, agglomerate and stick to surfaces.

Furthermore, the use of pelletized $NaHCO_3$ also overcomes several disadvantages that the use of bicarbonate powder has when used in a mechanically operated device. First, due to the fine particulate nature of powders, dust and fine particulates can enter the mechanical components of the dispensing device, cause failures due to build-up and collection on or around the mechanical components of the device. Since $NaHCO_3$ is a very hard, abrasive substance, use of $NaHCO_3$ powder therefore is abrasive and its dust can cause premature wear and aging of mechanical parts and components of the powder dispensing system. Second, in a humid environment, powders can absorb the moisture in the system and become agglomerated and form clumps, which can clog or block the $NaHCO_3$ dispenser openings, preventing the $NaHCO_3$ powder from reaching the reactive acid solution and thus causing device failure and unreliability. Anti-clumping additives may be used to counteract this, but this addition results in added weight to the system.

The $CO_2$ generator of the present invention provides a device for controlling flow rate of $CO_2$ (via an algorithm and a high accuracy in measuring the actual dispensing of pellets). The use of pellets allows for a highly accurate $CO_2$ flow rate based on size, weight and/or density of the pellets and the controlled rate at which they are dispensed.

The pellets used in the device can be various shapes of pellets known in the art including cylinders, spheres, oblong bodies, discs, cubes, or any other reproducible shape for mass-produced pellets. For use in our device, pellets may be any reproducibly agglomerated or compacted form of bicarbonate powder or granules that when reacted with acid produces $CO_2$ gas. The resulting pellet should be reproducible in terms of weight, size and density. Methods of pelletization of bicarbonate can include, but are not limited to, compaction, disc agglomeration, layering, globulation, spray drying, spray congealing, extrusion, balling, granulation (fluid-bed and rotary), and other common methods known to A Person Having Ordinary Skill In The Art.

Additionally, pellets may contain additives to help with the pelletization process. Such additives can act as binders to hold the pellets together or function as solid lubricants, to keep powder free flowing during pelletization and to reduce friction during compaction/pelletization techniques. Binders and solid lubricants may be present in the pellets at levels from 0.05-5 wt %, depending on the agglomeration method used to produce the pellets. Such additives that function as binders may include, but are not limited to waxes, magnesium stearate, starches, lignin, cellulosic binders, clays, polymeric binders, and others used in the art. Additives that function as solid lubricants may include, but are not limited to, talc, metallic (magnesium) stearates, hexagonal boron nitride (HBN), amide waxes, polytetrafluoroethylene (PTFE), tungsten disulfide, and others that are known to A Person Having Ordinary Skill In The Art.

The pellets preferably comprise a bicarbonate salt chosen from sodium bicarbonate, lithium bicarbonate, potassium bicarbonate, ammonium bicarbonate, magnesium bicarbonate, calcium bicarbonate strontium bicarbonate or combinations thereof. Optionally, the pellets may also comprise a carbonate salt chosen from sodium carbonate, lithium carbonate, potassium carbonate, ammonium carbonate, magnesium carbonate, calcium carbonate strontium carbonate or combinations thereof.

Pellet sizes are preferably from ⅛ inch up to ⅜ inch, but typically at most 0.5 inches. In a preferred embodiment the pellets are ¼ inch diameter×¼ inch long cylinders. Regardless of the pellet size, control of the pellet weight is critical for the successful metering of the bicarbonate into the aqueous acid solution. In an embodiment of the present invention the pellets each have a mass within 15 weight percent of the arithmetic mean, more preferably within 10 weight percent of the arithmetic mean, even more preferably at most within 7 weight percent of the arithmetic mean. In a non-limiting example, the pellets have an average weight of 0.43 grams per pellet with a standard deviation of 0.03 grams (or 7 percent deviation).

Aqueous acid solution used in the reaction chamber:

The acid used for reaction with the bicarbonate in the reactor chamber can be any acid that is dosed to the reactor in an amount that will supply reactant for the bicarbonate pellets over the programmed operation period, typically 12 hours. The acid is diluted with a water source, not necessarily potable, to form a liquid acid solution for dosed bicarbonate pellets to react with. Acids may include one or more acids, wherein at least one of the one or more acids is chosen from acetic acid, ascorbic acid, butanoic acid, citric acid, formic acid, heptanoic acid, hexanoic acid, 1-octanoic acid, lactic acid, octanoic acid, oxalic acid, pentanoic acid, propanoic acid, uric acid, succinic acid, malonic acid, maleic acid, citriconic acid, norbornene dicarboxylic acid, gamma-hydroxy butanoic acid, benzoic acid, boric acid, sulfuric acid, hydrochloric acid, nitric acid, phosphoric acid, linear or branched $C_1$-$C_{20}$ alkane sulfonic acids, linear or branched $C_2$-$C_{20}$ alkene sulfonic acids, $C_6$-$C_{20}$ substituted or unsubstituted aryl sulfonic acids or combinations thereof. Optionally, the acid may comprise, ammonium bisulfate, other bisulfate salts (sodium, lithium, potassium).

Preferably, the acid consists of a solid, non-hazardous, transportation-safe organic acid (safe at room temperature) that can be dissolved in water prior to use and originally be stored as a solid. Such acids include, but are not limited to, citric acid, maleic acid, malic acid, malonic acid, propionic acid, butanoic acid, pentanoic acid, hexanoic acid, heptanoic acid, and octanoic acid.

Furthermore, many organic acids that are solid at room temperature have endothermic heats of solution that cause a severe temperature drop in the acid solution when they are dissolved in water. This drop in solution temperature for the starting aqueous acid solution can affect the rate at which $CO_2$ is produced from the reaction of bicarbonate with acid once the device in is use, therefore affecting the performance of the device and the ability to produce $CO_2$ gas at a rate that will keep up with the programmed flow rate. Therefore, any of the solid acids listed above may be mixed with a solid additive that will maintain acid solution temperature neutrality, or result in a rise in temperature, upon dissolution of the acid plus additive.

The use of the additive to regulate starting solution temperature provides better control of the rate of $CO_2$ generation and offsets reaction rate decreases caused by temperature decreases due to the endothermic evolution of a gas (carbon dioxide). Such additives may include inorganic compounds that have known exothermic heats of solution. These include but are not limited to anhydrous magnesium chloride ($MgCl_2$), magnesium chloride monohydrate ($MgCl_2.H_2O$), anhydrous calcium chloride ($CaCl_2$), and calcium chloride dihydrate ($CaCl_2.2H_2O$). Additive amounts can be added to the acid formulation as needed to offset the temperature decrease observed upon dissolving the needed amount of acid, typically in the range of 3 weight percent to 20 weight percent. In a preferred embodiment the additive is anhydrous $MgCl_2$, or partially hydrated $MgCl_2$.

Other mechanical and electronic embodiments of the invention:

The device provides a self-unclogging or self-clearing dispensing hole. During use, it is possible for two or more pellets to be positioned at the entrance to the dispensing hole in such a manner that they do not fall through the hole under the force of gravity. This phenomenon may be referred to as "bridging" by the pellets across the hole. The hole size cannot be too small relative to the pellet size because this would make the dispensing too slow, as a single rotation of the feeder may not result in the dispensing of one or more pellets. If the hole is too large relative to the pellet size it may dispense too many at once. The preferred diameter of the hole is between 1.75 and 2.35 times the diameter of the pellet, more preferably the hole is between 1.75 and 1.95 times the diameter of the pellet, and most preferably the hole is 1.88 times the diameter of the pellet or the largest dimension of the pellet for non-spherical pellets. As an example, when the pellets are ¼ inch diameter by ¼ inch long cylinders the preferred dispensing hole diameter is 0.47 inches (which is 1.88 times the diameter of the pellet). This will lead to occasional bridging or clogs by the pellets, since more than one 0.25 inch cylindrical pellet cannot fit through a 0.47 inch diameter dispensing hole simultaneously. The present invention solves this problem by rotating the feeder. The portion of the feeder with the hole will become inverted and the bridged pellets will fall away and back into the feeder. On the next rotation the hole may dispense one or more pellets. The means for counting dispensed pellets (for example the sound bar) allows the device to accurately know how many pellets have fallen out of the feeder and into the reaction chamber (and the aqueous acid solution). In preferred embodiments the feeder reservoir has a diameter of between 6 and 7 inches when ¼ inch diameter by ¼ inch long cylinder pellets are used. In an optional embodiment, the feeder reservoir has a diameter of between 4.5 and 5 inches when ¼ inch diameter by ¼ inch long cylinder pellets are used. In a most preferred embodiment, the feeder reservoir has a diameter of 6.77 inches when ¼ inch diameter by ¼ inch long cylinder pellets are used in combination with a 0.47 inch dispensing hole.

The present invention comprises a means for controllably adding pellets from the feeder reservoir to the reaction chamber. In one embodiment the means for controllably adding pellets comprises a rotating feeder having one or more dispensing holes and a servo motor to accurately rotate the feeder. Other electrically or mechanically driven motors or devices to generate rotational motion in an accurate manner may be substituted for the servo motor. The means further comprises a programmed electronic circuit or equivalent component or device that is operably connected to the servo motor or equivalent. In an optional embodiment, the electronic circuit (or equivalent) may be operably connected to a microphone sensor (or equivalent) and it can determine the number of pellets dispensed based on the sound the pellets make from hitting a sound bar positioned between the feeder reservoir and the reaction chamber.

In an optional embodiment, the device comprises a sound-based counting system. This includes a sound bar, and a microphone sensor (or equivalent) that are mechanically mounted in the device, and wherein, the sound bar is positioned between the feeder reservoir and the reaction chamber such that when in use, pellets dispensed from the feeder reservoir impact the sound bar. The microphone sensor is suitable for detecting the noise from the sound bar and accurately identifying each pellet dispensed from the feeder. In an optional embodiment the sound-base counting system further comprises a resonant sound board that is connected to the sound bar. The resonant sound board is positioned in close proximity to the microphone sensor. In further optional embodiments, the sound system is sound-insulated from outside noise. In a more preferred embodiment the resonant sound board and the microphone sensor are insulated from outside noise. In yet another optional embodiment, the microphone sensor is a noise-cancelling microphone, where the noise cancellation process works by utilizing a second microphone to pick up unwanted noise, modifying the phase angle of the sound by 180 degrees, and then adding it to the sound output of the initial signal; the two perfectly out of phase wave forms cancel themselves out, leaving only distinct signal from the pellet being dispensed. The use of the noise cancelling microphone differentiates the sound emanating from the sound bar or the resonant sound board from noises originating from outside the device or from the noise caused by moving parts of the device itself.

Figure 2:
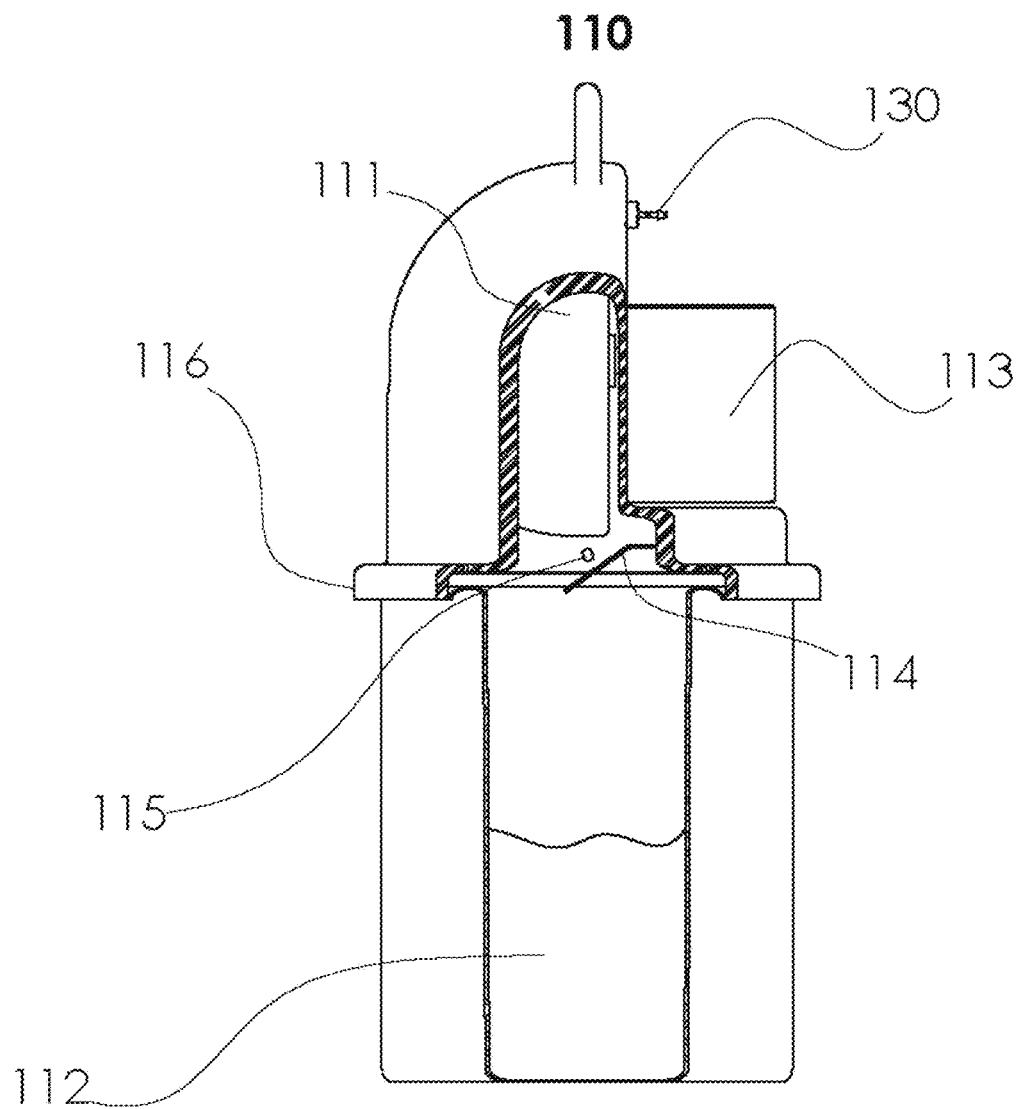
FIG. 2. Humidity tolerant $CO_2$ generator.
Figure 3:
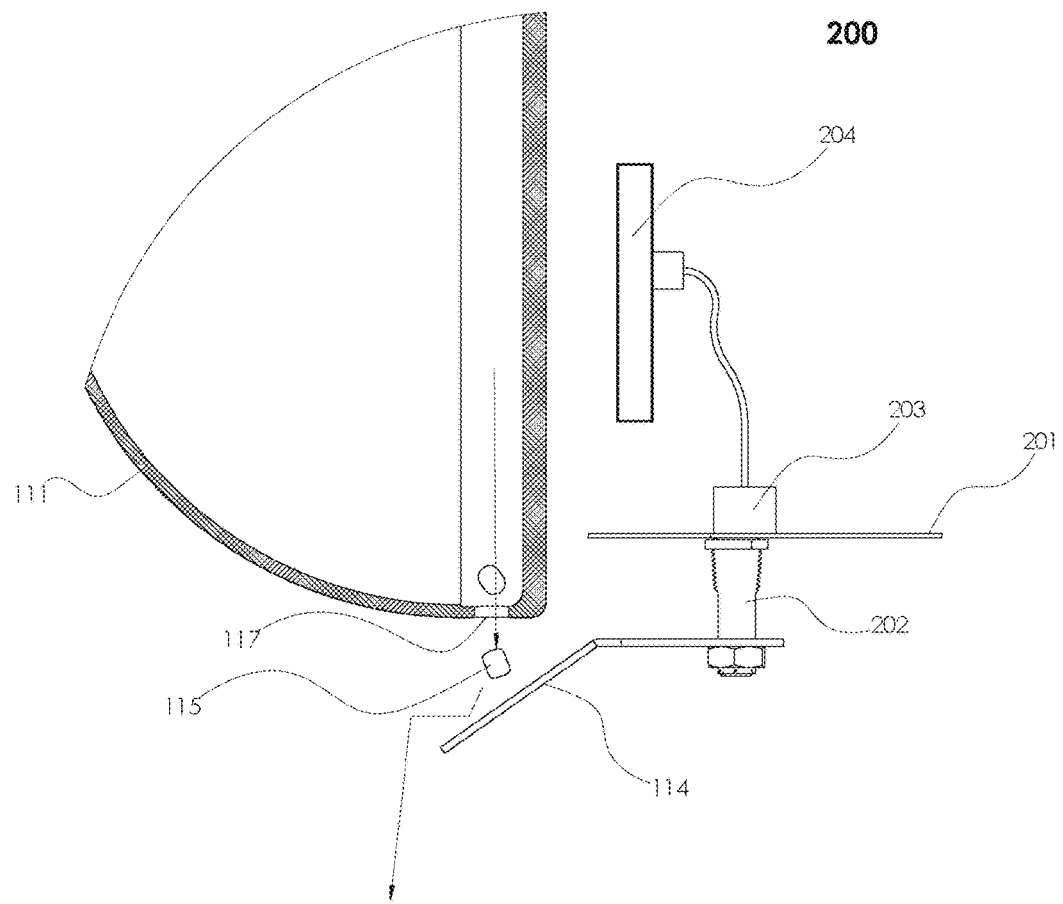
FIG. 3. Feeder reservoir and sound-based pellet counting system.
Figure 4:
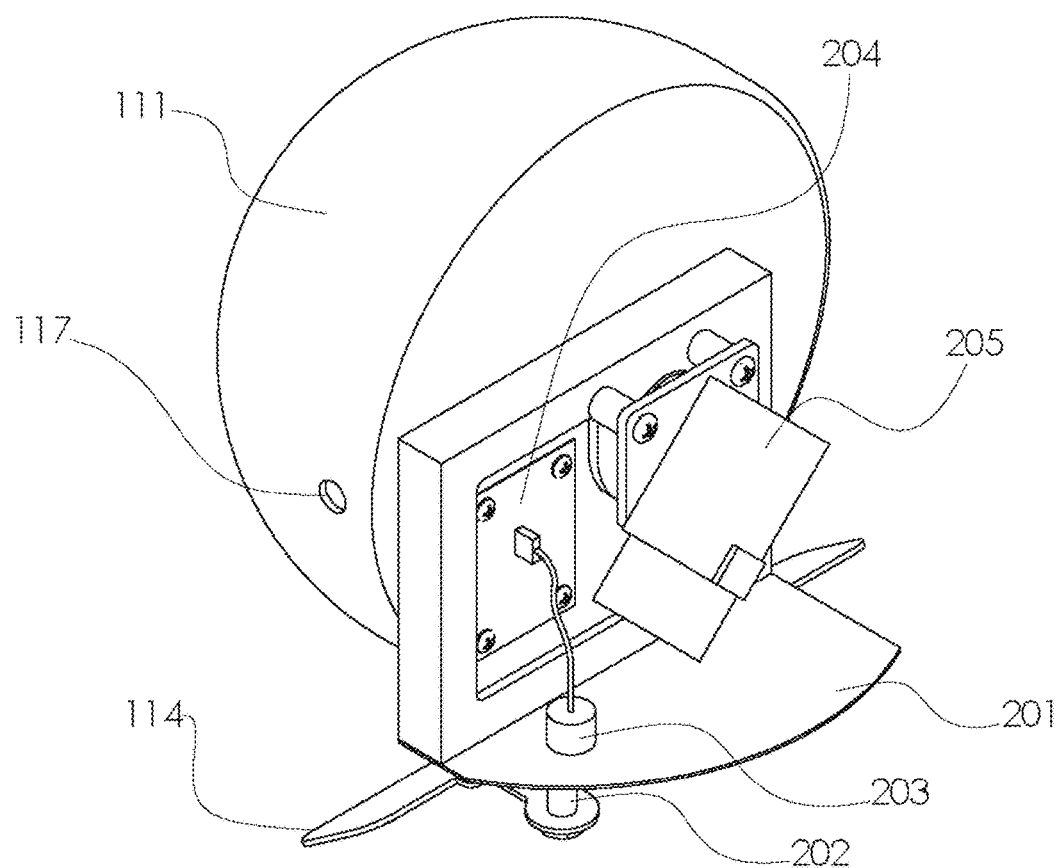
FIG. 4. Preferred embodiment of the means for controllably dispensing pellets from the feeder reservoir.
Figure 5:
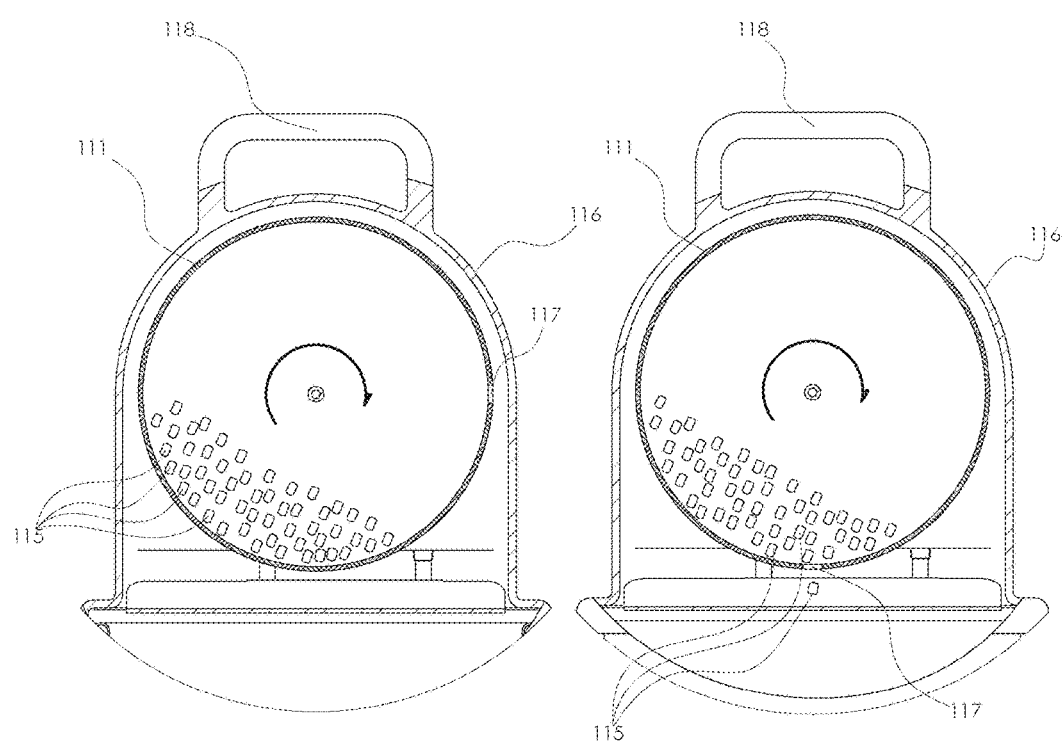
FIG. 5. Rotating feeder reservoir.
Figure 6:
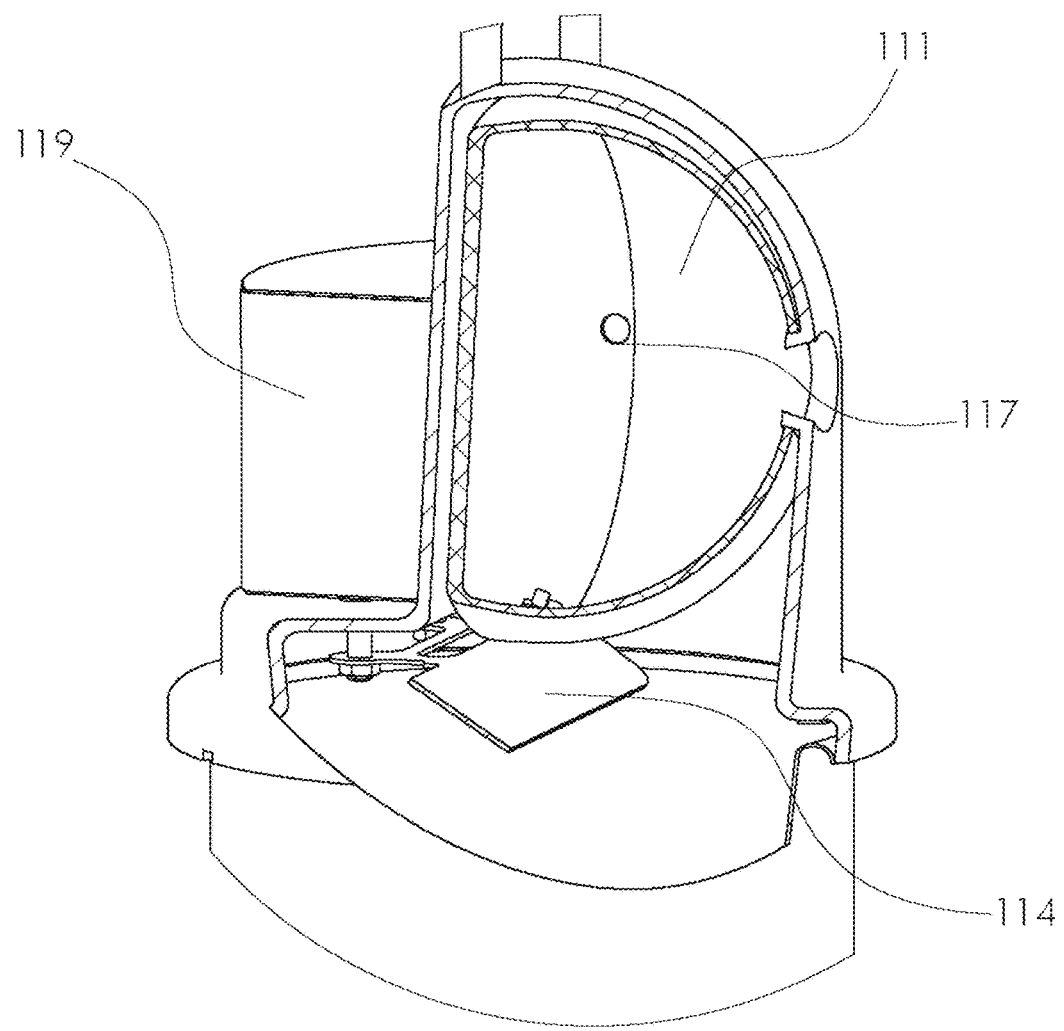
FIG. 6. Rotating feeder reservoir combined with a sound-based pellet counting system.
Figure 7:
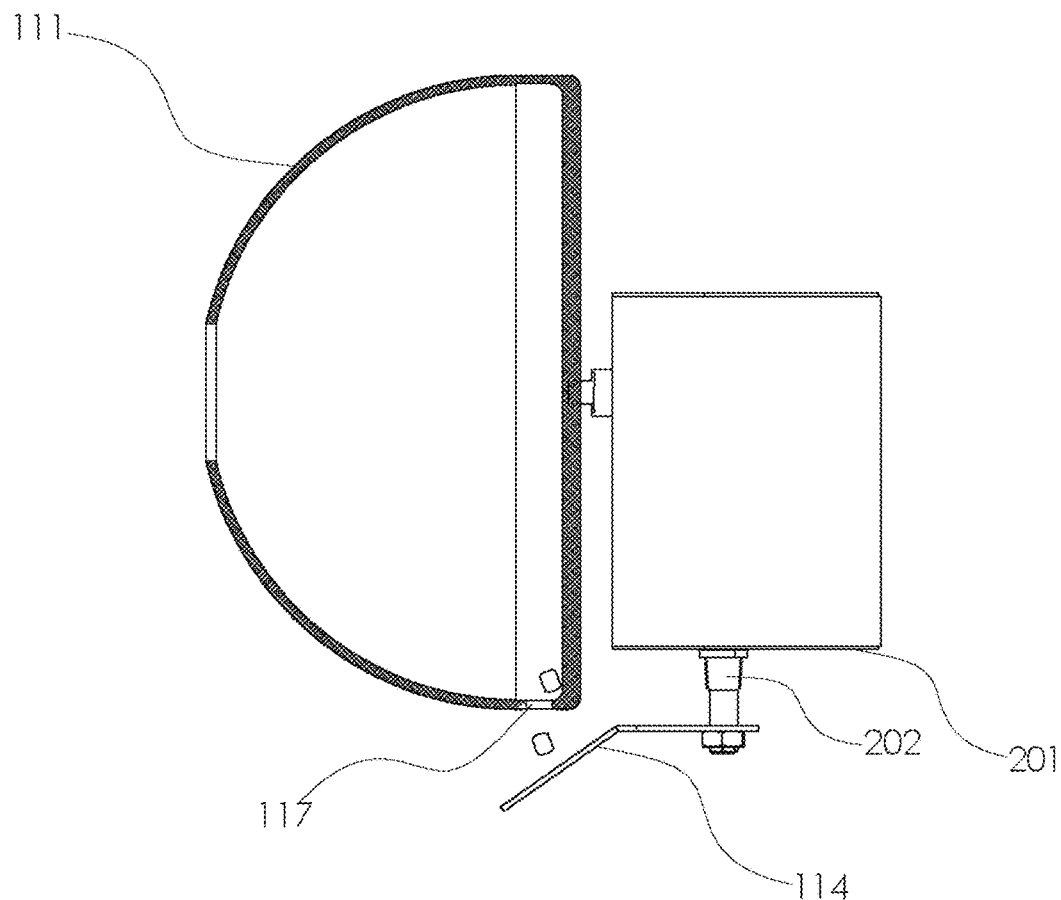
FIG. 7. Hemispherical feeder reservoir with sound bar counter.
Figure 8:
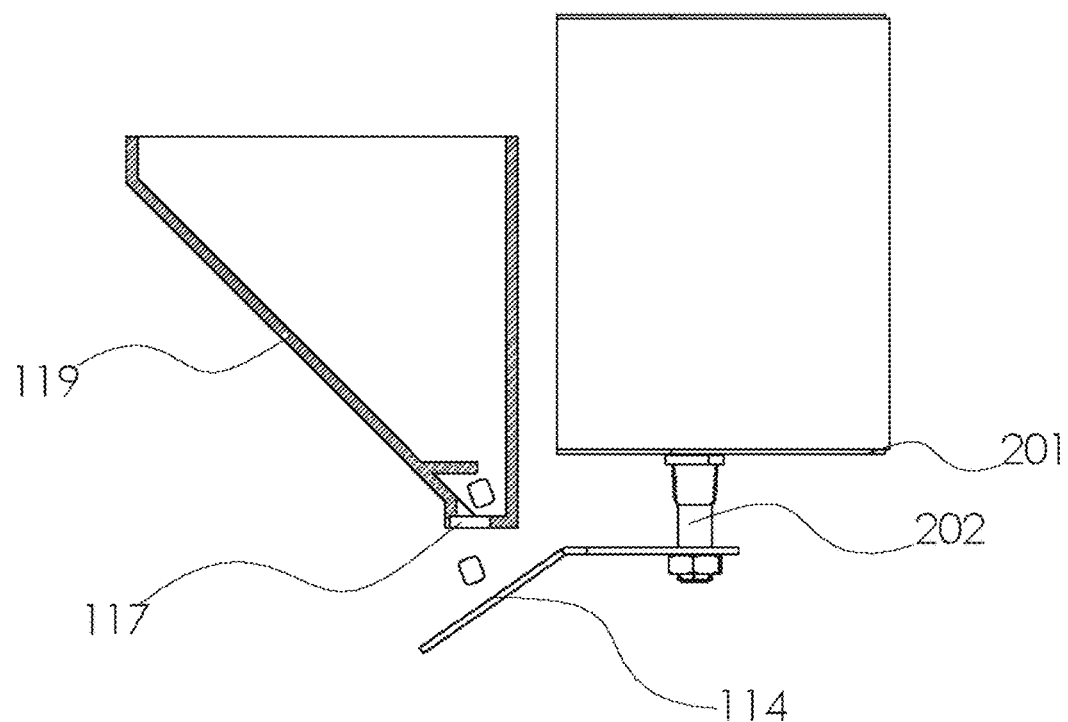
FIG. 8. Conical feeder reservoir with sound bar counter.
Figure 9:
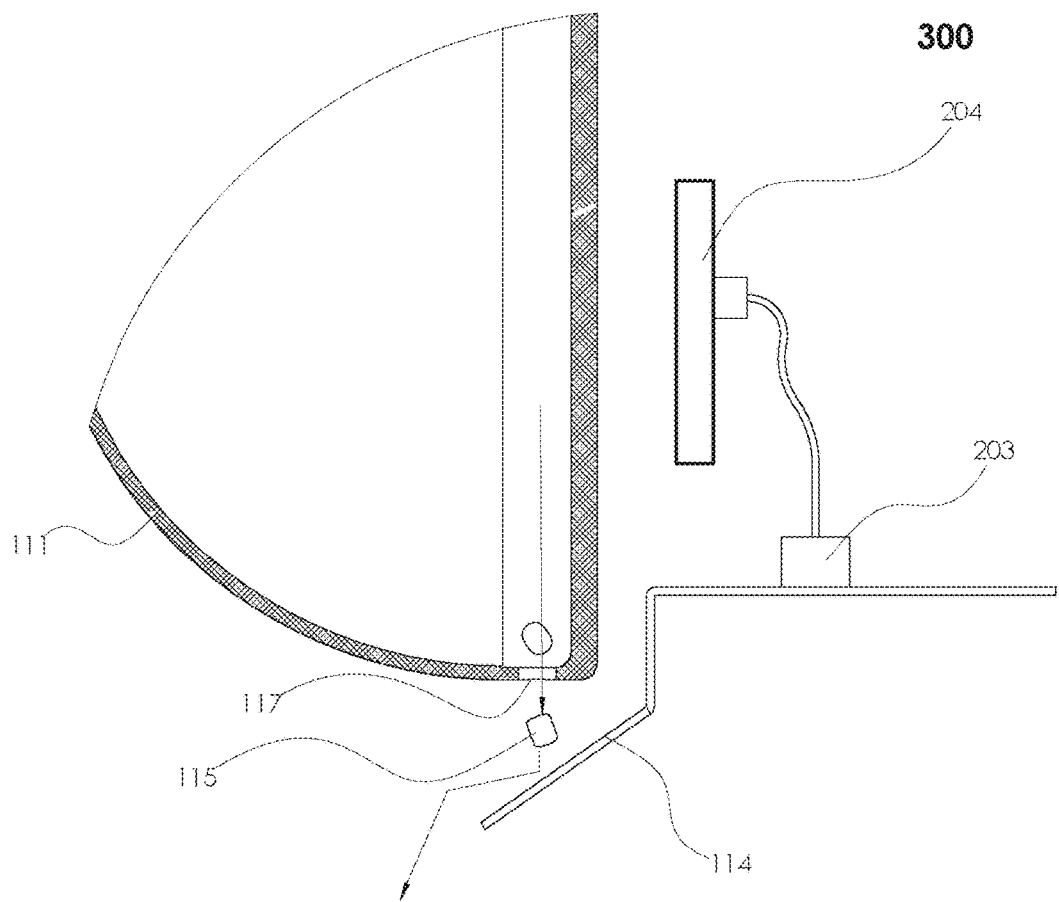
FIG. 9. Rotating feeder reservoir combined with a simplified sound-based pellet counting system.

With reference to FIG. 1, the device for generating carbon dioxide 110 as an attractant for biting arthropods is used in combination with a trap 120, and the two are connected by a gas outlet 130 (i.e. a tube or conduit for $CO_2$ gas that is generated by the device for generating carbon dioxide 110 to be sent to the trap 120). With reference to FIG. 2, The device for generating carbon dioxide 110 comprises a feeder reservoir 111 (inside the feeder reservoir is contained the plurality of pellets), a reaction chamber charged with an aqueous acid solution 112, and a means for controllably adding pellets from the feeder reservoir to the reaction chamber. In FIG. 2, the means for controllably adding pellets from the feeder reservoir to the reaction chamber is illustrated as a housing 113 that contains a motor and an electronic circuit (not shown in FIG. 2, but shown in FIG. 4). A sound bar 114 is positioned between the feeder reservoir and the reaction chamber so that pellets 115 strike the sound bar after falling from the feeder reservoir. The device contains an airtight housing 116, such that when $CO_2$ is generated by the reaction chamber it is forced out via the gas outlet 130 and to an insect trap. FIG. 3 shows additional embodiments of the device, in particular a sound-based counting system 200 to accurately count pellets dispensed from a feeder reservoir, which can be used as part of a means for controllably adding the pellets from the feeder reservoir to a reaction chamber (for example, accurate counting is needed to know how many pellets are added at a given time). The sound-based counting system is used in combination with a feeder reservoir 111, where pellets 115 fall onto a sound bar 114. The sound bar is connected (via a solid material component 202) to a resonant sound board 201, which can effectively transmit sound waves to a microphone sensor 203. The microphone sensor is operably connected to an electronic circuit 204 as optionally part of a means for controllably adding the pellets from the feeder reservoir to a reaction chamber. In FIG. 4, a preferred embodiment for the means for controllably adding pellets from a feeder reservoir (and into a reaction chamber which is not shown) comprises a hemispherical feeder reservoir 111, a dispensing hole 117, a sound bar 114, a solid support 202 connecting the sound bar to a resonant sound board 201, a microphone sensor 203 operably connected to an electronic circuit 204, which is further operably connected to a servo motor 205. The servo motor (or equivalent) controllably rotates the feeder reservoir. FIG. 5 illustrates a rotating feeder reservoir 111 at two different angular orientations. The plurality of pellets 115 are tumbled inside the reservoir during operation. The dispensing hole 117 rotates with the feeder reservoir such that when it is located down (in direction of gravity) pellets may fall through. If pellets become stuck in the dispensing hole, via bridging etc., the hole will become cleared once rotated 180 degrees, and on the top of the feeder reservoir, where they can fall back into the center of the feeder reservoir. The view also contains a carrying handle 118. FIG. 6 shows a rotating feeder reservoir 111 with a dispensing hole 117 operably connected to a sound bar and a sound insulating housing 119. Not shown, inside the housing is a resonant sound board and microphone sensor. FIGS. 7 and 8 show optional variants of a rotating feeder reservoir. In FIG. 7 a hemispherical feeder reservoir 111 had a dispensing hole 117, a sound bar 114, and a solid support 202 connecting the sound bar to a resonant sound board 201. In FIG. 8 a conical feeder reservoir 119 had a dispensing hole 117, a sound bar 114, and a solid support 202 connecting the sound bar to a resonant sound board 201.

Example 1, exemplary pellet preparation method: Prior to pressing pellets, we first mixed the powdered pellet precursor formulation consisting of $NaHCO_3$ (baking soda) with 0.10 weight percent magnesium stearate (binder) and 0.05 weight percent hexagonal boron nitride (HBN; solid lubricant). To perform this mixing efficiently, all powders are mixed by hand to form an initial mixture. The initial mixture is then sieved three times through a 60 mesh screen to ensure uniform mixing throughout the pellet precursor powder. The resulting powder is then pressed into 0.25 inch diameter by 0.25 inch high cylindrical pellets using a Rotary Pellet Press using techniques standard to the art.

Alternatively, a formulation consisting of $NaHCO_3$ with 0.15 weight percent magnesium stearate (binder and lubricant) can be mixed using a paddle mixer to prepare the initial powder. The initial powder can then be sieved three times through a 60 mesh screen to form the pellet precursor powder. The resulting powder is then pressed into 0.25 inch diameter by 0.25 inch high cylindrical pellets using a Rotary Pellet Press using techniques standard to the art.

Example 2, exemplary acid powder preparations: To prepare the acid formulation, 50 lbs of malic acid is mixed with 5 lbs of anhydrous magnesium chloride (MgCl) using a large-scale rotary powder mixer. The powder mixture is mixed at high speed for 20 minutes. Alternatively, 50 lbs of citric acid is mixed with 12 lbs of calcium chloride ($CaCl_2$) using a large-scale rotary powder mixer. The powder mixture is mixed at high speed for 20 minutes. Other acid mixtures include 50 lbs. malic acid with 14 lbs $CaCl_2$, or 50 lbs. citric acid with 4.5 lbs $MgCl_2$.

Example 3, in this example the device represented by FIGS. 1-6 is used. The top portion of the device contains the pellet dispensing mechanism, electronic controller for the dispensing mechanism, and the gas outlet. The bottom portion of the device is the reactor, which contains the acid solution. In this version, the pellet dispensing mechanism consists of a motor-operated rotary feeder, that is controlled electronically, and a pellet counting mechanism consisting of a sound bar and a microphone that records the sound of each individual pellet hitting the sound bar as the pellet is dispensed. The diameter of the feeder reservoir is 6.77 inches. The dispensing hole diameter is 0.47 inches. In this non-limiting example, 1150 g of acid mixture consisting of malic acid containing 8 weight % anhydrous $MgCl_2$ was added to 3 liters of water in the reactor. The rotary dispenser was filled with 1150 g of cylindrical sodium bicarbonate pellets (radius ¼ inch×¼ inch height) with an average weight of 0.43 grams per pellet with a standard deviation of 0.03 grams (or 7 percent deviation) and a pellet composition of 0.05 weight percent hexagonal boron nitride, 0.10 weight percent magnesium stearate, and 99.85 weight % sodium bicarbonate. The pellets were dispensed to the acid solution from the dispenser that was controlled electronically by an electronic circuit executing a control algorithm with input from the pellet counting mechanism.

Figure 10:
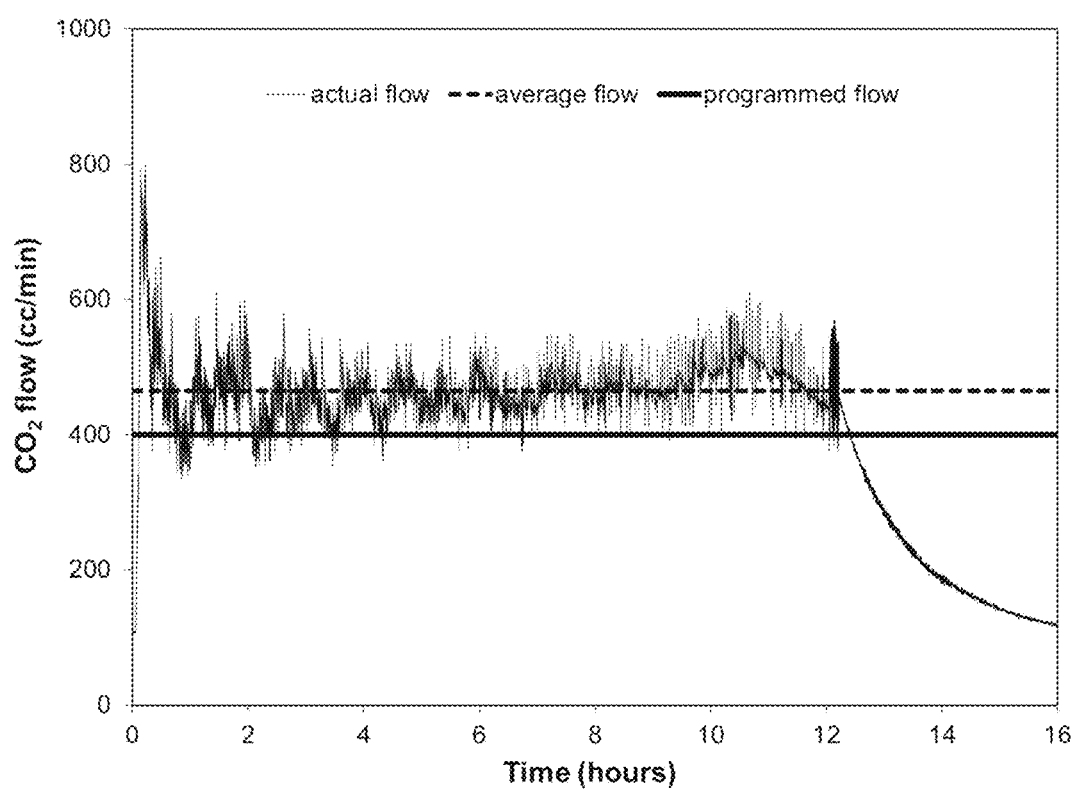
FIG. 10. $CO_2$ flowrate generated in Example 3.

The device in Example 3 generated $CO_2$ by pre-programming the control algorithm to produce a flow rate of 400 mL/minute and allowing the device to run until all bicarbonate pellets were dispensed. The gas flow rate was measured using a mass flow meter at 23° C. Based on the amount of chemicals loaded into the device, the 400 mL/minute run was designed to operate for 12-13 hours at the programmed flow rate. The result of the run is shown in FIG. 10. The 12-hour average flow rate produced was 465 mL/minute of $CO_2$. The steady, gradual decrease in flow at greater than 12 hours is due to remaining bicarbonate continuing to react and being released from the device until the chemicals are spent.

Figure 11:
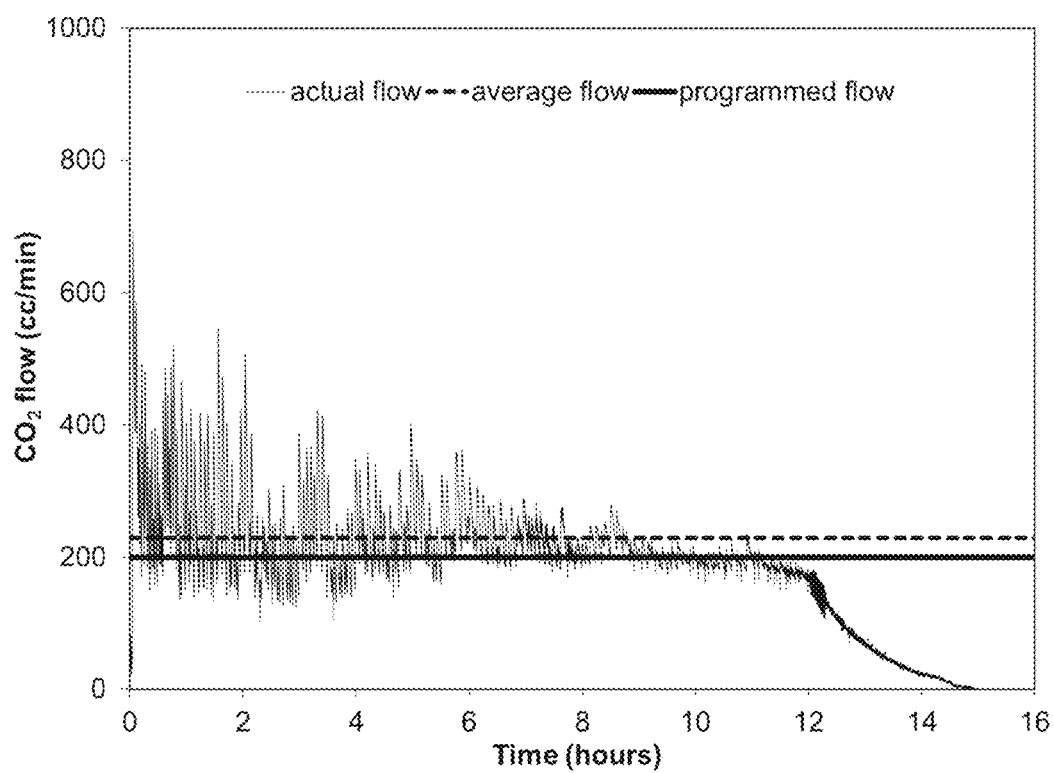
FIG. 11. $CO_2$ flowrate generated in Example 4.

Example 4, using the same device as in Example 3 but the programmed flow rate was 200 mL/minute and the programmed run time was set at 12 hours. The result of the run is shown in FIG. 11. The 12-hour average flow rate produced was 229 mL/minute of $CO_2$. The steady, gradual decrease in flow at greater than 12 hours is due to remaining bicarbonate continuing to react and being released for the device until the chemicals are spent.

Figure 12:
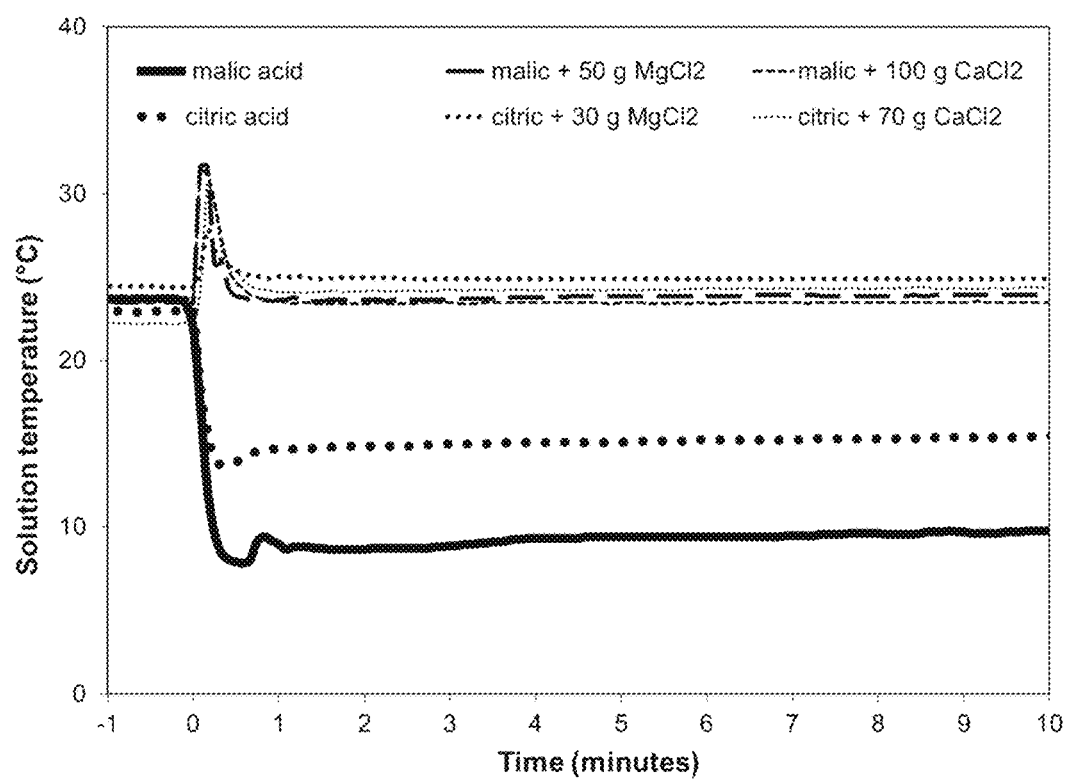
FIG. 12. $CO_2$ flowrate generated in Example 5.

Example 5, using the device of Example 3 with an acid that has an additive to offset the temperature decrease caused by dissolving an acid with an endothermic heat of solution. The additive may be an inorganic salt that has an exothermic heat of solution that results in solution temperature neutrality or an increase in temperature. In this example, 500 grams of malic acid or citric acid was dissolved in 1 liter of water without any additive (FIG. 12) to demonstrate the temperature drop of the solution when acids with endothermic heats of solution are dissolved. While the magnitude of the temperature drop will vary with the volume of water used and the amount of acid dissolved, it can be seen that a temperature drop in solution can be on the magnitude of 10-20 degrees C., a significant decrease that can affect reaction rates. In contrast, the temperature decrease can be offset by adding a reasonable amount of a salt with an exothermic heat of solution to the acid prior to dissolving. In this example, 30 and 50 grams of anhydrous magnesium chloride ($MgCl_2$) were added to 500 grams of citric and malic acids, respectively, and 70 and 100 grams of anhydrous calcium chloride ($CaCl_2$) were added to citric and malic acid, respectively. FIG. 12 shows that solid mixtures of acid and salts result in temperature neutrality (i.e., the solution temperature is the same prior to and following dissolving of acid/salt mixtures) following dissolution of the solid mixture in one liter of water, after a brief spike in solution temperature. Addition of larger amounts of exothermic dissolving salts can also raise the temperature of the starting acid solution.

Example 6, This is an example of using the device of Example 3 with a bicarbonate pellet produced by compaction and containing 0.05-5 weight percent magnesium stearate binder and 0.05-5 weight percent hexagonal boron nitride solid lubricant, preferably 0.05 weight percent hexagonal boron nitride and 0.10 weight percent magnesium stearate. Pellets were produced by compaction using a RB2 Stokes rotary tablet press equipped with 16 stations for pressing pellets and providing 2 to 4-ton compression per station. Pellets produced are ¼" diameter by ¼" height with densities of 2.1 g/cc (7% variability). Prior to making pellets, a pellet precursor powder consisting of the desired pellet formulation (bicarbonate+lubricant+binder) was mixed by sieving the powder mixture together using a Sweco vibratory separator to ensure that the ingredients are well mixed. Following the mixing of the precursor powders, pellets are then pressed using the Stokes rotary pellet press.

Although the present invention has been described in considerable detail with reference to certain preferred versions thereof, other versions are possible. Therefore, the spirit and scope of the appended claims should not be limited to the description of the preferred versions contained herein, except where required by 35 U.S.C. § 112 ¶ 6 or 35 U.S.C. § 112 (f).

The reader's attention is directed to all references which are filed concurrently with this specification and which are incorporated herein by reference.

All the features in this specification (including any accompanying claims, abstract, and drawings) may be replaced by alternative features serving the same, equivalent or similar purpose, unless expressly stated otherwise. Thus, unless expressly stated otherwise, each feature disclosed in one example only of a generic series of equivalent of similar features. Any element in a claim that does not explicitly state "means for" performing a specified function, or "step for" performing a specific function, is not to be interpreted as a "means" or "step" clause as specified in 35 U.S.C. § 112 ¶ 6 or 35 U.S.C. § 112 (f). Any element in a claim that does explicitly state "means for" performing a specified function, or "step for" performing a specific function, is to be interpreted as a "means" or "step" clause as specified in 35 U.S.C. § 112 ¶ 6 or 35 U.S.C. § 112 (f).

What is claimed is:

1. A device for generating carbon dioxide as an attractant for biting arthropods in combination with a trap, comprising:
   (a.) a reaction chamber charged with an aqueous acid solution when in use;
   (b.) a trap for biting arthropods;
   (c.) a gas outlet from the reaction chamber connecting between the reaction chamber and the trap for biting arthropods;
   (d.) a feeder reservoir containing a plurality of pellets when in use, said pellets comprising a bicarbonate salt;
   (e.) means for controllably adding the pellets from the feeder reservoir to the reaction chamber; whereby carbon dioxide is generated in the reaction chamber, passed through the outlet and into the trap for biting arthropods;
   (f.) a sound bar;
   (g.) a microphone sensor; and
   (h.) means for counting the pellets added to the reaction chamber when in use.

2. The device of claim 1, further comprising:
   (i.) a resonant sound board connected to the sound bar; and
   (j.) a sound absorbing material surrounding the microphone sensor and the resonant sound board;
      wherein, the resonant sound board is physically attached to the sound bar and transfers sound from the sound bar to the microphone sensor; and, wherein the sound absorbing material reduces external noise reaching the microphone sensor.

* * * * *